US011337589B2

(12) United States Patent
Hatano et al.

(10) Patent No.: US 11,337,589 B2
(45) Date of Patent: May 24, 2022

(54) BENDING OPERATION DEVICE AND ENDOSCOPE

(71) Applicant: Olympus Corporation, Hachioji (JP)

(72) Inventors: Keisuke Hatano, Koganei (JP); Kiwamu Fujitani, Orefield, PA (US)

(73) Assignee: OLYMPUS CORPORATION, Tokyo (JP)

(*) Notice: Subject to any disclaimer, the term of this patent is extended or adjusted under 35 U.S.C. 154(b) by 233 days.

(21) Appl. No.: 16/131,671

(22) Filed: Sep. 14, 2018

(65) Prior Publication Data
US 2019/0014974 A1   Jan. 17, 2019

Related U.S. Application Data

(63) Continuation of application No. PCT/JP2016/077266, filed on Sep. 15, 2016.

(30) Foreign Application Priority Data

Mar. 24, 2016 (JP) ................. 2016-060365

(51) Int. Cl.
A61B 1/005 (2006.01)
G02B 23/24 (2006.01)
A61B 1/00 (2006.01)

(52) U.S. Cl.
CPC .......... *A61B 1/0057* (2013.01); *A61B 1/0052* (2013.01); *A61B 1/00066* (2013.01);
(Continued)

(58) Field of Classification Search
CPC .............. A61B 1/0057; A61B 1/00066; A61B 1/00165; A61B 1/0052; A61B 1/00043;
(Continued)

(56) References Cited

U.S. PATENT DOCUMENTS

2011/0295068 A1   12/2011 Petersen et al.
2012/0302832 A1*  11/2012 Inada ................. A61B 1/00039
                                             600/118
(Continued)

FOREIGN PATENT DOCUMENTS

JP   2001-054501    2/2001
JP   2004-248777    9/2004
(Continued)

OTHER PUBLICATIONS

International Search Report and Written Opinion from corresponding International Application No. PCT/JP2016/077266, dated Nov. 15, 2016.
(Continued)

Primary Examiner — Michael J Carey
Assistant Examiner — Christen A. Sharpless
(74) Attorney, Agent, or Firm — Oliff PLC

(57) ABSTRACT

A bending operation device includes a bending operation lever, a wire pulling member, bending operation wires, and tubular members. The bending operation lever is tiltably supported to have an angle with respect to a longitudinal direction of an operation unit of an endoscope. The wire pulling member includes arm portions displaced in conjunction with tilt motion of the bending operation lever. The bending operation wires are connected to the arm portions. The bending operation wires cause bending motion of a bendable part disposed in an insertion section of the endoscope. A respective one of bending operation wires is inserted in each of the tubular members. The tubular members (i) change extension directions of the plurality of bending operation wires and (ii) guide the plurality of bending operation wires to the plurality of arm portions.

16 Claims, 12 Drawing Sheets

(52) U.S. Cl.
CPC ...... *A61B 1/00165* (2013.01); *G02B 23/2423* (2013.01); *G02B 23/2476* (2013.01); *A61B 1/00043* (2013.01); *A61B 1/00071* (2013.01); *A61B 1/00131* (2013.01)

(58) Field of Classification Search
CPC ............ A61B 1/00071; A61B 1/00131; G02B 23/2423; G02B 23/2476
USPC ........................................................ 600/147
See application file for complete search history.

(56) References Cited

U.S. PATENT DOCUMENTS

| | | | |
|---|---|---|---|
| 2013/0047757 A1 | 2/2013 | Okamoto et al. | |
| 2013/0112457 A1* | 5/2013 | Kitagawa | A61B 1/0056 174/68.3 |
| 2013/0197309 A1* | 8/2013 | Sakata | A61B 1/00114 600/132 |
| 2014/0066716 A1* | 3/2014 | Arai | A61B 1/0057 600/149 |
| 2014/0309625 A1 | 10/2014 | Okamoto et al. | |
| 2016/0029878 A1 | 2/2016 | Yamazaki et al. | |
| 2016/0227986 A1 | 8/2016 | Yasunaga et al. | |
| 2016/0309985 A1 | 10/2016 | Akui | |
| 2017/0007224 A1 | 1/2017 | Sholev et al. | |

FOREIGN PATENT DOCUMENTS

| | | | | |
|---|---|---|---|---|
| JP | 2005-066128 | | 3/2005 | |
| JP | 2010214043 A | * | 9/2010 | |
| JP | 2012-511356 | | 5/2012 | |
| JP | 2015-104627 | | 6/2015 | |
| JP | 2016-034352 | | 3/2016 | |
| WO | 2010066789 | | 6/2010 | |
| WO | 2012117835 | | 9/2012 | |
| WO | 2013108776 | | 7/2013 | |
| WO | WO-2014192447 A1 | * | 12/2014 | ........... A61B 1/0057 |
| WO | 2015068468 | | 5/2015 | |
| WO | 2015151093 | | 10/2015 | |
| WO | 2015174139 | | 11/2015 | |

OTHER PUBLICATIONS

Japanese Office Action No. JP2017-521168, dated Nov. 27, 2017.
Japanese Office Action No. JP2017-521168, dated Jul. 24, 2017.

* cited by examiner

BENDING OPERATION DEVICE AND ENDOSCOPE

CROSS-REFERENCE TO RELATED APPLICATIONS

This application is a continuation application of PCT Application No. PCT/JP2016/077266 filed on Sep. 15, 2016, which in turn claim priority to the Japanese Patent Application No. 2016-060365 filed on Mar. 24, 2016 in Japan which is hereby incorporated by reference in its entirety.

TECHNICAL FIELD

The technology disclosed herein generally relates to a bending operation device and an endoscope that cause the bending motion of a bendable part in conjunction with a tilt operation to a bending operation lever.

DESCRIPTION OF THE RELATED ART

In the past, in order to diagnose a place inside a subject, such as inside of a biological body and/or inside of a structural object, which is difficult to do so, various endoscopes that can be inserted in the subject have been widely used in e.g. the medial field or the industrial field.

In an insertion section of such an endoscope, a bendable part is provided for improving the insertability and observation performance of the inside of the subject. Bending operation of this bendable part is carried out by a bending operation device disposed in an operation unit.

For example, in International Patent Publication No. WO2012/117835, a joystick-type tubular operation device is disclosed as the bending operation device for carrying out bending operation of the bendable part of the insertion section. Regarding the existing bending operation device, a technique has been disclosed. In the technique, the bending operation device includes an electric motor that rotates a pulley around which a midway part of a bending operation wire is wound in a loosened state. The operation device causes motion of the bendable part. The purpose for this technique is reducing the amount of operation force to pull the bending operation wire connected to the joystick-type bending operation lever.

Incidentally, the existing endoscope includes the joystick-type bending operation lever in the operation unit like that disclosed in the International Patent Publication No. WO2012/117835. In typical endoscope, built-in parts are generally disposed inside. The built-in parts are for various kinds of endoscope functions, such as a cylinder to which a suction valve is mounted. Incidentally, in order to reduce the size of the operation unit, the arrangement needs to be made in such a manner that the movable range of the joystick-type bending operation lever does not interfere with the built-in parts such as a cylinder. Furthermore, generally the tiltable angle of the joystick-type bending operation lever is limited and therefore it is necessary to sufficiently ensure the amount of pulling/loosening of the bending operation wire. Moreover, in the handy-type endoscope, it is desirable that (i) the bending operation lever be disposed at a position decided in consideration of the operability of tilting of the bending operation lever by a hand that grips the operation unit and (ii) the amount of pulling/loosening of multiple bending operation wires with respect to the amount of displacement due to tilt operation of the bending operation lever be made constant.

A neutral state is a state in which the bendable part of the insertion section is in a straight-line state. If the joystick-type bending operation lever is disposed such that to be tilted toward the operation unit in the neutral state, there is a problem that it becomes impossible to obtain a constant amount of wire pulling/loosening with respect to the displacement of the bending operation lever. Moreover, in the existing endoscope including the joystick-type bending operation lever in the operation unit, there is a problem that the size of the operation unit becomes larger to ensure the amount of wire pulling to bend the bendable part to a desired bending angle.

BRIEF SUMMARY OF EMBODIMENTS

A bending operation device according to one aspect of the present disclosure includes a bending operation lever, a wire pulling member, a plurality of bending operation wires, a plurality of tubular members, first attaching members, and second attaching members. The bending operation lever is tiltably supported to have an angle with respect to a longitudinal direction of an operation unit of an endoscope. The wire pulling member has a plurality of arm portions being displaced in conjunction with tilt motion of the bending operation lever. The wire pulling member is disposed in the operation unit. The plurality of bending operation wires are connected to the plurality of arm portions so as to cause bending motion of a bendable part disposed in an insertion section of the endoscope by being pulled or loosened corresponding to displacement of the wire pulling member. The plurality of bending operation wires are extended in respective predetermined directions in the operation unit. A respective one of the plurality of bending operation wires is inserted in each of the plurality of tubular members. The plurality of tubular members have respective tip portions and proximal parts. The tip portions accept the plurality of bending operation wires oriented in the respective predetermined directions. The tip portions are oriented in the respective predetermined directions. The proximal parts are on a proximal side relative to the tip portions and are disposed to change extension directions of the plurality of bending operation wires. The plurality of tubular members causes the plurality of bending operation wires to become substantially parallel when the bending operation lever is at a neutral position. The bendable part is in a substantially straight line manner when in the neutral position. The respective tip portions and the proximal parts are disposed in the operation unit. The plurality of tubular members guide the plurality of bending operation wires disposed substantially parallel to the plurality of arm portions. The first attaching members attach the tip portions of the plurality of tubular members in the operation unit in such a manner as to orient the tip portions in the respective predetermined directions. The second attaching members attach the proximal parts of the plurality of tubular members in the operation unit in such a manner that the proximal parts become substantially parallel.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
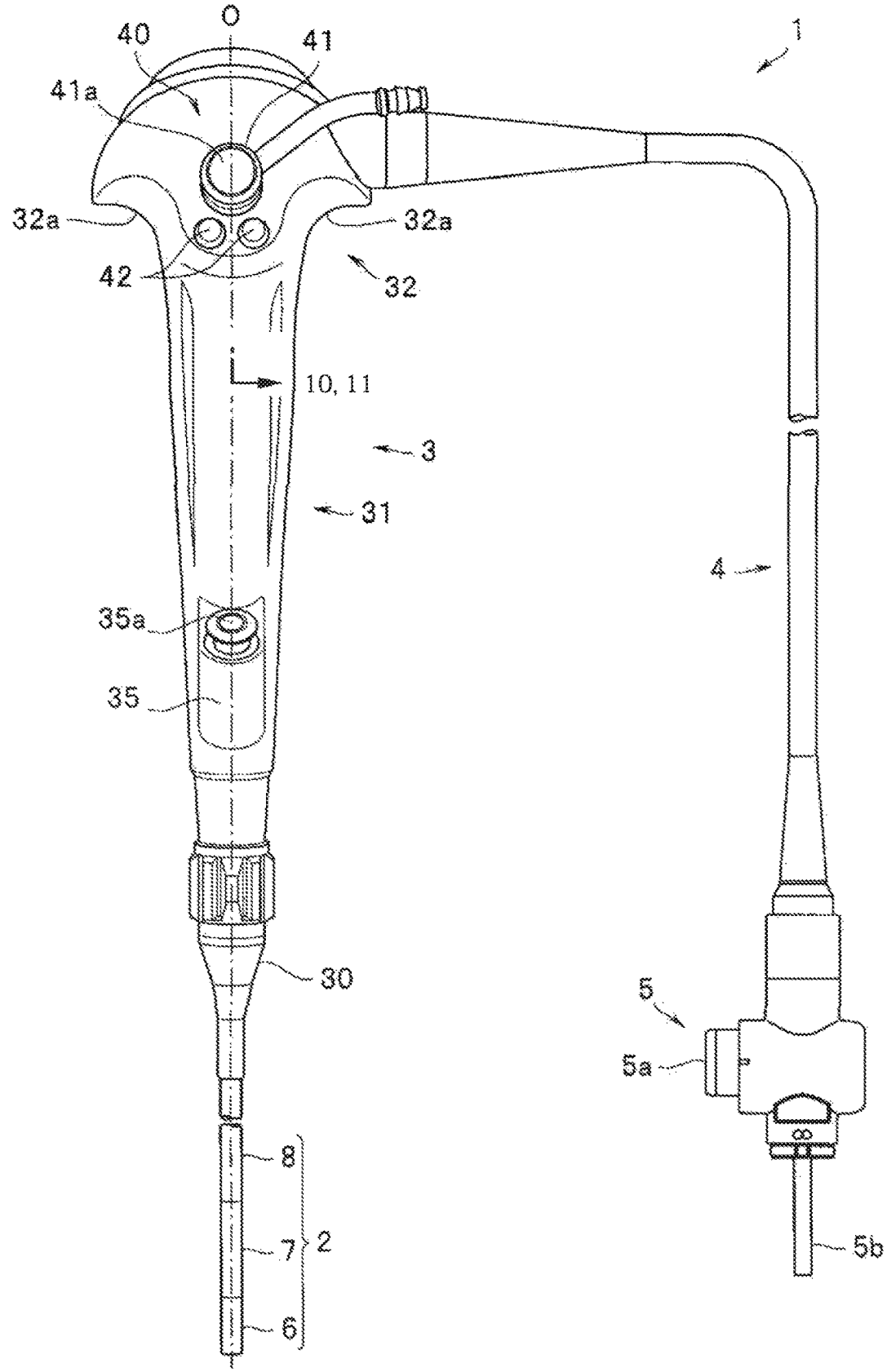
FIG. 1 is a front view of an endoscope having a bending operation device thereon according to an embodiment of the technology described herein.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The technology disclosed herein is made in view of the above-described circumstances and intends to provide a bending operation device and an endoscope with which (i) increase in the size of an operation unit is prevented and (ii) the amount of pulling/loosening of plural wires with respect to the amount of displacement by tilt of the bending operation lever becomes constant and (iii) the amount of pulling/loosening of the bending operation wire to bend the bendable part to a desired bending angle is stably obtained.

A bending operation device according to one aspect of the present disclosure includes a bending operation lever, a wire pulling member, a plurality of bending operation wires, and a plurality of tubular members. The bending operation lever is tiltably supported to have an angle with respect to a longitudinal direction of an operation unit of an endoscope. The wire pulling member is disposed in the operation unit. The wire pulling member includes a plurality of arm portions displaced in conjunction with tilt motion of the bending operation lever. The plurality of bending operation wires are connected to the plurality of arm portions. The plurality of bending operation wires cause bending motion of a bendable part disposed in an insertion section of the endoscope by being pulled or loosened according to displacement of the wire pulling member. A respective one of the plurality of bending operation wires is inserted in each of the plurality of tubular members. The plurality of tubular members (i) change extension directions of the plurality of bending operation wires and (ii) guide the plurality of bending operation wires to the plurality of arm portions. Therefore, the plurality of bending operation wires become substantially parallel when the bending operation lever is at a neutral position with which the bendable part is in a substantially straight line manner.

Furthermore, in an endoscope according to one aspect of the present disclosure, an operation unit is disposed in a bending operation device. The bending operation device includes a bending operation lever, a wire pulling member, a plurality of bending operation wires, and a plurality of tubular members. The bending operation lever is tiltably supported to have an angle with respect to a longitudinal direction of the operation unit. The wire pulling member is disposed in the operation unit. The wire pulling member includes a plurality of arm portions displaced in conjunction with tilt motion of the bending operation lever. The plurality of bending operation wires are connected to the plurality of arm portions. The plurality of bending operation wires cause bending motion of a bendable part disposed in an insertion section of the endoscope by being pulled or loosened according to displacement of the wire pulling member. A respective one of the plurality of bending operation wires is inserted in each of the plurality of tubular members. The plurality of tubular members (i) change extension directions of the plurality of bending operation wires and (ii) guide the plurality of bending operation wires to the plurality of arm portions. Therefore, the plurality of bending operation wires become substantially parallel when the bending operation lever is at a neutral position with which the bendable part is in a substantially straight line manner.

In the following description, it should be noted that the drawings based on the respective embodiments are schematic and the relationship between the thickness and width of each part, the ratio of the thicknesses of the respective parts, and so forth are different from actual ones, and parts different in the relationship and ratio of the respective dimensions also between the drawings are included in some cases.

Figure 2:
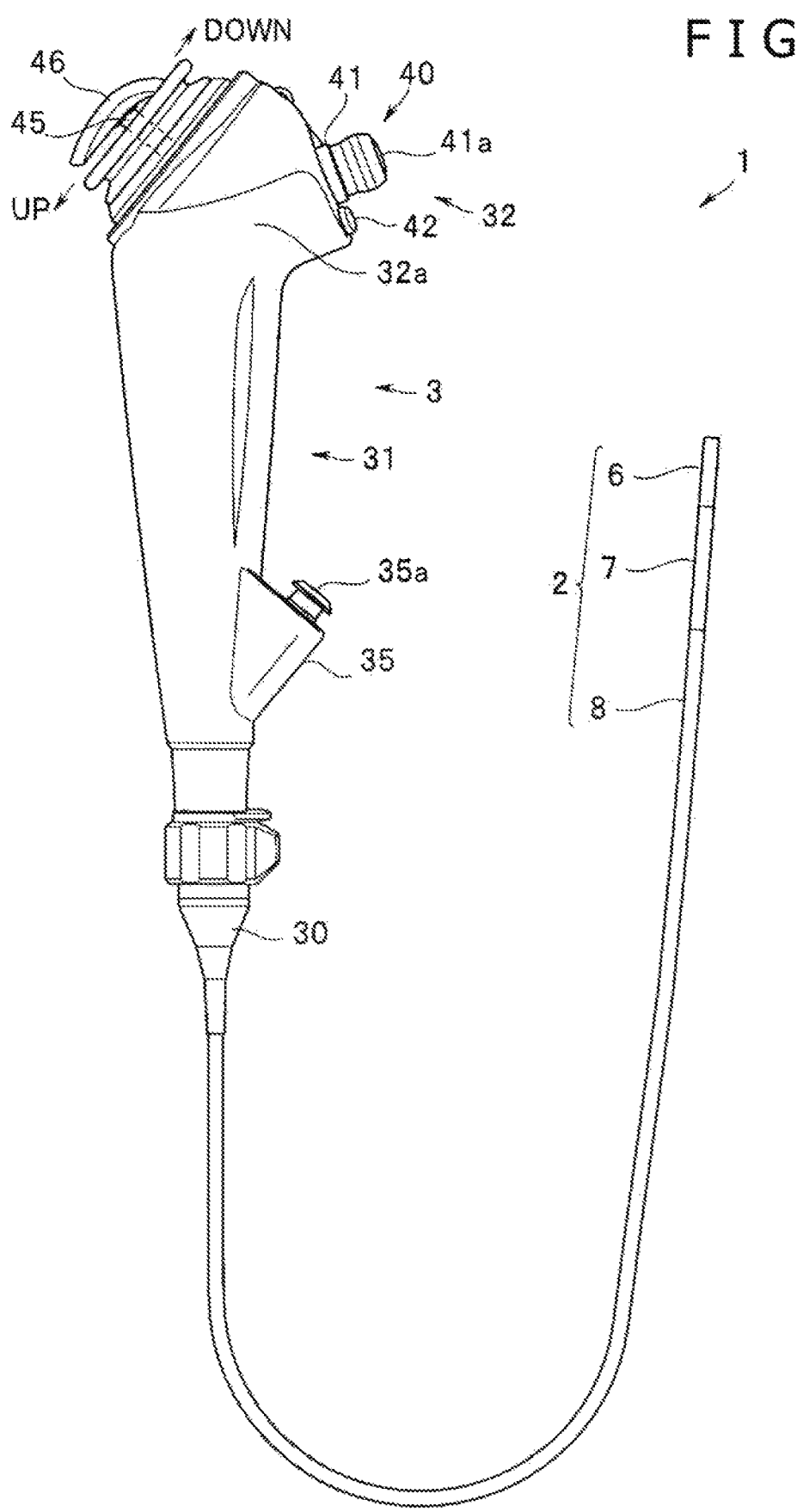
FIG. 2 is a right side view of the endoscope.

The endoscope of this embodiment is a bronchial endoscope 1. As illustrated in FIGS. 1 and 2, this endoscope 1 includes an insertion section 2, an operation unit 3, a universal cord 4, and an endoscope connector 5. The insertion section 2 is formed in the shape of a slender tube. The operation unit 3 is disposed consecutively on a proximal end of the insertion section 2. The universal cord 4 is used as an endoscope cable disposed extending from the operation unit 3. The endoscope connector 5 is disposed on a distal end of the universal cord 4.

The insertion section 2 is formed of a tube body having flexibility in which a tip portion 6, a bendable part 7, and a flexible tube part 8 are consecutively disposed in that order from the distal side. The operation unit 3 includes a bend preventing portion 30, a grip handle 31 and an operation unit main body 32. The bend preventing portion 30 is connected to the flexible tube part 8 in a state that the flexible tube part 8 is covered at a proximal end thereof with the bend preventing portion 30. The grip handle 31 is disposed consecutively with the bend preventing portion 30 and can be held by the user or the like. The operation unit main body 32 is disposed consecutively on the side of a proximal end of the grip handle 31. It is to be noted that in this embodiment, directions about an insertion axis "O" or the like in the operation unit 3 are defined based on a state that the user or the like holds the grip handle 31. Specifically, with respect to the operation unit 3, front, rear, left and right directions ("front" wall, "rear" wall and "left" and "right" walls, and so on) are defined as viewed from the user or the like who holds the grip handle 31.

As illustrated in FIG. 1, the grip handle 31 of the operation unit 3 is formed in a horizontally-symmetrical shape with respect to the insertion axis "O" or central axis. Therefore, the user or the like can similarly hold the grip handle 31 with either of left or right hand.

On a front wall on the side of a distal end of the grip handle 31, a surgical instrument insertion part 35 is disposed. This surgical instrument insertion part 35 includes a surgical instrument insertion port 35a. A surgical instrument (not shown) for a desired treatment site can be inserted through the surgical instrument insertion port 35a.

The operation unit main body 32 of the operation unit 3 has a shape that bulges to the left and right sides symmetrically with respect to the insertion axis "O". On left and right side walls on the side of a distal end of the operation unit main body 32, guide recesses 32a are formed to guide the index finger or the like of the user, who holds the grip handle 31, to operation buttons 40. The surgical instrument insertion port 35a is in communication with a surgical instrument insertion channel 13 via an unillustrated branch member inside the operation unit 3. The surgical instrument insertion channel 13 is described hereinafter in FIG. 4. Further, at the surgical instrument insertion part 35, an unillustrated forceps plug is detachably disposed. The forceps plug is a lid member for closing up the surgical instrument insertion port 35a.

On the side of the proximal end of the grip handle 31, the operation unit main body 32 is configured of a hollow member of a substantially partial-spherical shape that bulges primarily to the left and right sides and also frontward. On the side of a front wall of the operation unit main body 32, the operation buttons 40 are formed to perform various functions of the endoscope 1. These buttons 40 include, for non-limiting example, a suction button 41a and two button switches 42. The suction button 41a projects from a suction valve 41 detachably attached to the operation unit main body 32. Desired ones of the various functions of the endoscope 1 can be allocated to the two button switches 42. These suction button 41a and button switches 42 are arranged so that they become horizontally symmetrical on the side of the front wall of the operation unit main body 32.

Described specifically, the suction button 41a in this embodiment is arranged centrally in the horizontal width direction of the operation unit main body 32 so that the suction button 41a lies on the insertion axis "O".
On the other hand, the two button switches 42 are arranged at horizontally symmetrical positions, with the insertion axis "O" being flanked therebetween, on a side more distal than the suction button 41a.

Figure 3:
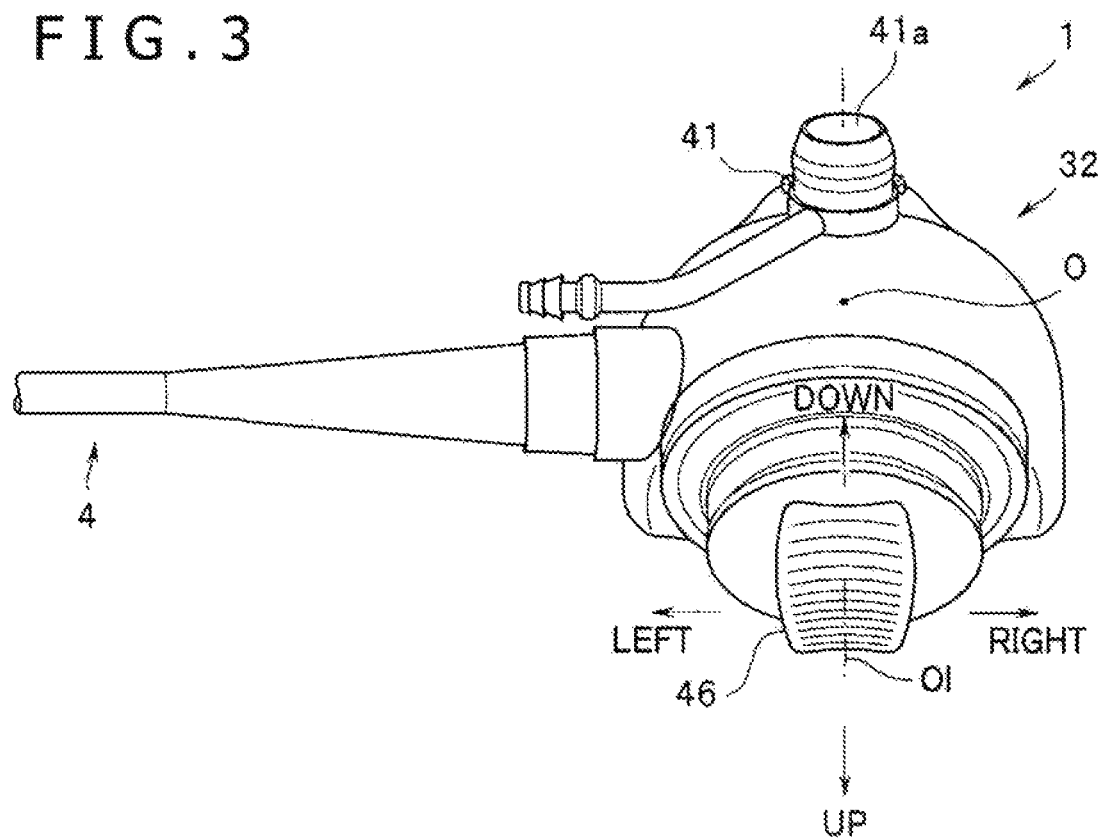
FIG. 3 is a top view of the endoscope.

As illustrated in FIG. 2 and FIG. 3, on the side of the rear wall of the operation unit main body 32, a joystick-type bending operation lever 45 is disposed (not illustrated in FIGS. 1 and 3) as a bending operation lever for use in performing bending operation on the bendable part 7. As the direction of tilting of the bending operation lever 45, as illustrated in FIG. 3, for example, the left-right direction of tilting operation is defined in the horizontal width direction of the operation unit 3. The horizontal width direction is a direction orthogonal to the insertion axis "O". The up-down direction is defined in a direction orthogonal to the horizontal width direction. More specifically, leftward tilting direction, rightward tilting direction, upward tilting direction, and downward tilting direction are depicted as examples of the direction of tilting of the bending operation lever 45 in this embodiment. Direction to the left side of the sheet of FIG. 3 is defined to be the direction of tilting as the leftward tilting direction for bending the bendable part 7 leftward. Direction to the right side of the sheet of FIG. 3 is defined to be the direction of tilting as the rightward tilting direction for bending the bendable part 7 rightward. Direction to the lower side of the sheet of FIG. 3 is defined to be the direction of tilting as the upward tilting direction for bending the bendable part 7 upward. Direction to the upper side of the sheet of FIG. 3 is defined to be the direction of tilting as the downward tilting direction for bending the bendable part 7 downward.

A finger rest 46 is arranged on a pointed end portion of the bending operation lever 45. The thumb or the like of the user or the like can be kept in contact with the finger rest 46. From a side part (for example, the left side part) of this operation unit main body 32, the universal cord 4 extends. This universal cord 4 is a composite cable. Various signal lines and the like are (i) internally inserted through the universal cord 4, (ii) extending through the insertion section 2 from the side of the tip portion 6 to the operation unit 3 and (iii) further extending from the operation unit 3. A light guide 12 of a light source device (not illustrated) is inserted through the universal cord 4. An air-feed/water-feed tube is also inserted through the universal cord 4 and extending from an air-feed/water-feed device (not illustrated).

The endoscope connector 5 is disposed on a distal end of the universal cord 4 in FIG. 1. The endoscope connector 5 has an electric connector adapter 5a on a side wall part thereof. The endoscope connector 5 also has a light source connector adapter 5b. A signal cable is to be connected to the electric connector adapter 5a. The signal cable serves to connect between a video processor (not illustrated) as an external device and the electric connector adapter 5a. On the other hand, the light guide and electric cables are connected to the light source connector adapter 5b. The light guide helps to connect between the light source device as an external device and the light source connector adapter 5b.

Figure 4:
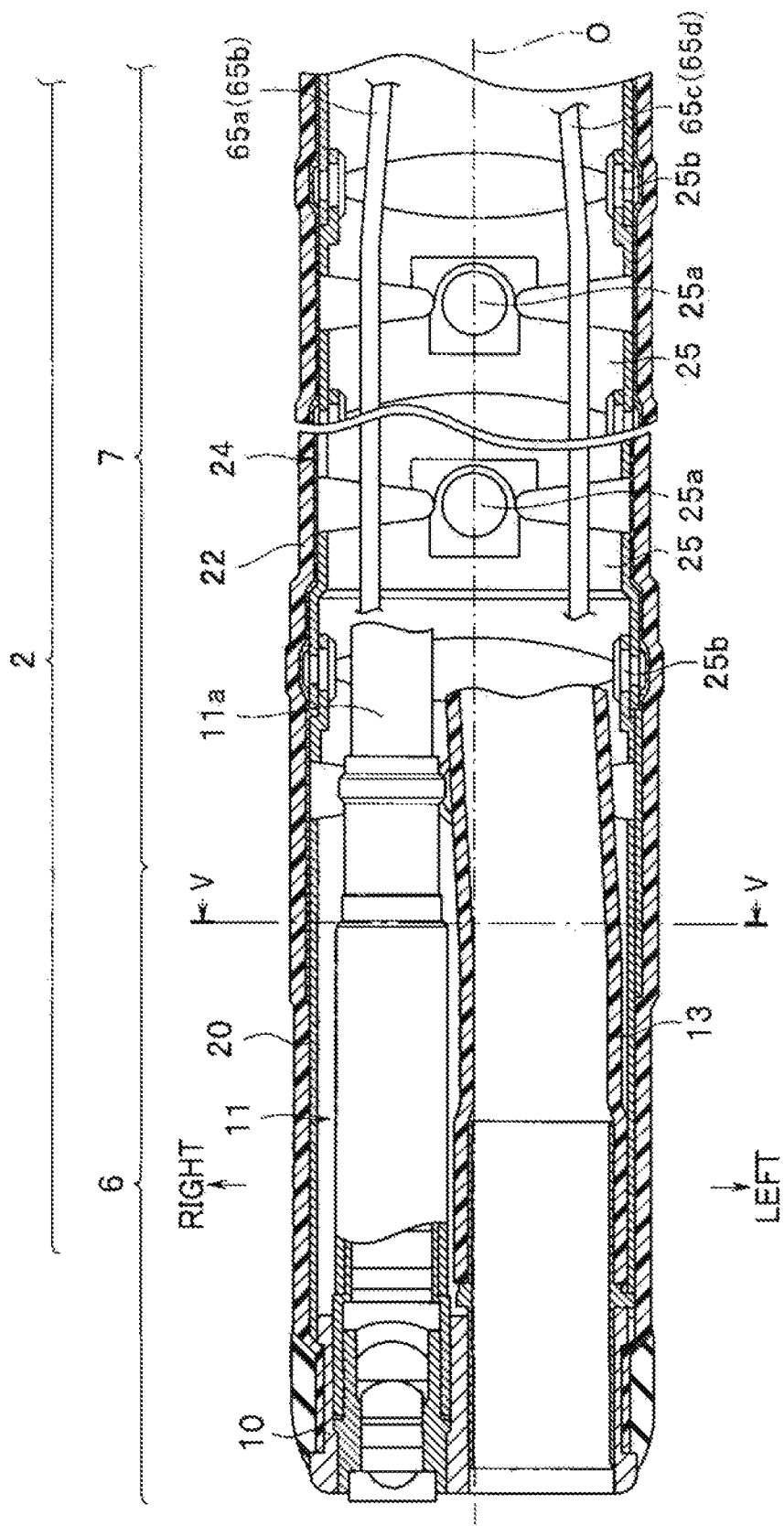
FIG. 4 is a cross-sectional view depicting the major part of a tip portion and a bendable part.
Figure 5:
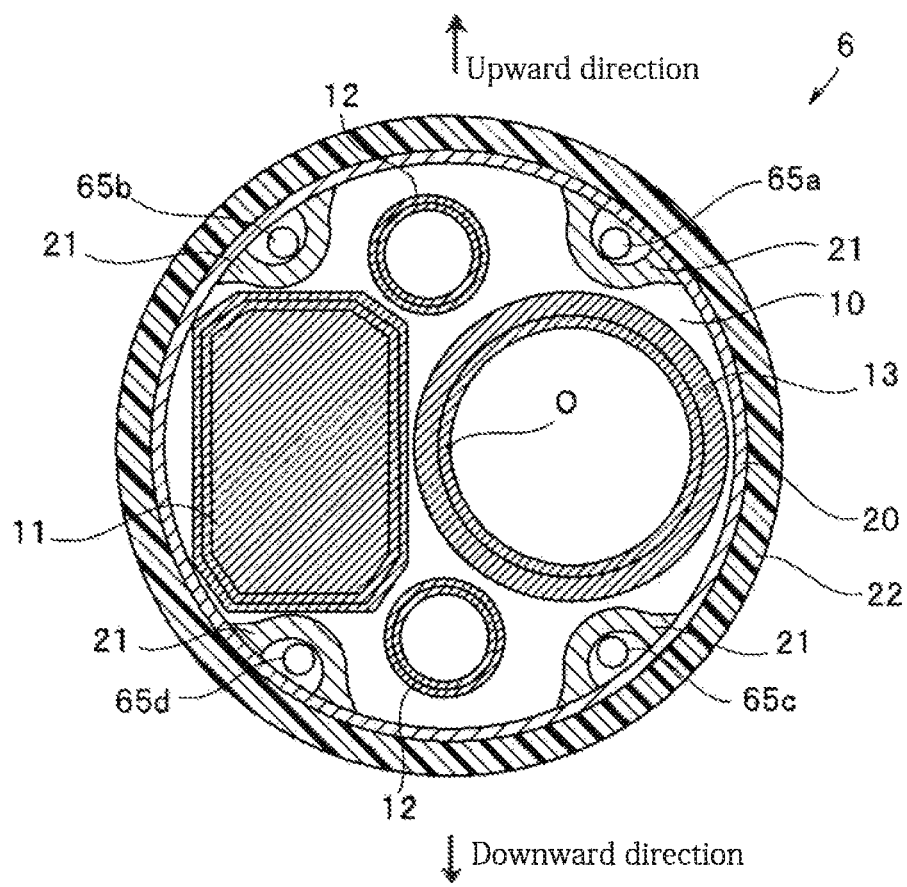
FIG. 5 is a sectional view depicting the tip portion along line V-V in FIG. 4.

As illustrated in FIG. 4 and FIG. 5, a metal-made, hard tip portion 10 is disposed in the tip portion 6. In this hard tip portion 10, (i) an imaging unit 11 with an imaging device such as CCD or CMOS accommodated therein, (ii) a pair of light guides 12 and (iii) the surgical instrument insertion channel 13 are held. In the tip portion 6, a most distal bending element 20 of a substantially cylindrical shape is externally fitted on the side of a proximal end of the hard tip portion 10. The most distal bending element 20 is covered at an outer circumference thereof with a bending rubber 22. On an inner circumference of the most distal bending element 20, wire anchors 21 are disposed at four locations about the insertion axis "O". On the respective wire anchors 21, pulling wires are inserted in the insertion section 2. Each of four bending operation wires 65a, 65b, 65c, and 65d are attached at any distal end thereof as pulling wires.

The imaging unit 11 and the surgical instrument insertion channel 13 are large-size members. Here, in order to efficiently dispose the respective constituent members without increasing the diameter of the tip portion 6, the imaging unit 11 and the surgical instrument insertion channel 13 are disposed to be arranged right and left in the hard tip portion 10 and the most distal bending element 20. Also, the light guides 12 are disposed in spaces formed on the upper and lower sides due to the position of the imaging unit 11 and the surgical instrument insertion channel 13. Furthermore, the respective wire anchors 21 are disposed at positions resulting from rotational movement around the insertion axis "O" by a predetermined angle with respect to upper, lower, right, and left positions of the tip portion 6 in order to avoid the interference between the imaging unit 11 and the surgical instrument insertion channel 13, and the respective bending operation wires 65a, 65b, 65c, and 65d.

Specifically, for example, as depicted in FIG. 5, on the most distal bending element 20, the respective wire anchors 21 are provided at (i) positions resulting from rotational movement around the insertion axis "O" in a range of 30 to 60 degrees regarding both in right and left based on the upward direction of the tip portion 6 and (ii) positions resulting from rotational movement around the insertion axis O in a range of 30 to 60 degrees regarding both in right and left based on the downward direction of the tip portion 6. The bendable part 7 is configured to be actively bendable in all directions around the insertion axis "O", including up-down/right-left directions, according to operational inputs to the operation unit 3 by a user or the like. Described specifically, the bendable part 7 in this embodiment is configured including a set 24 of bending elements. Multiple bending elements 25 are connected by alternately interposing pivots 25a and pivots 25b. The pivots 25a are disposed in the up-down direction of the insertion section 2. The Pivots 25b are disposed in the left-right direction of the insertion section 2.

A signal cable 11a, the light guides 12, and the surgical instrument insertion channel 13 all of which are inserted inside the set 24 of bending elements. The signal cable 11a, the light guides 12, and the surgical instrument insertion channel 13 are arranged in substantially the same arrangement as in the tip portion 6. The signal cable 11a extends from the imaging unit 11.

The predetermined one or more of the bending elements 25 make up the set 24 of bending elements. The respective bending operation wires 65a, 65b, 65c, and 65d are inserted through the wire guides (not illustrated). On each of the predetermined one or more of the bending elements 25, the wire guides are formed at positions where the arrangement of the wire guides in the direction of rotation about the insertion axis "O" is substantially the same as the above-described individual wire anchors 21. In addition, the set 24 of bending elements is covered at an outer circumference thereof with the bending rubber 22. The bending rubber 22 extends from the side of the tip portion 6. The flexible tube part 8 is configured of a tubular member having passively bendable flexibility. Inside this flexible tube part 8, signal cable 11a, the light guides 12 and the surgical instrument insertion channel 13 are inserted. In here, none of them is depicted.

Next, the configurations of individual components accommodated in the operation unit 3 will be described in detail hereinafter.

Figure 6:
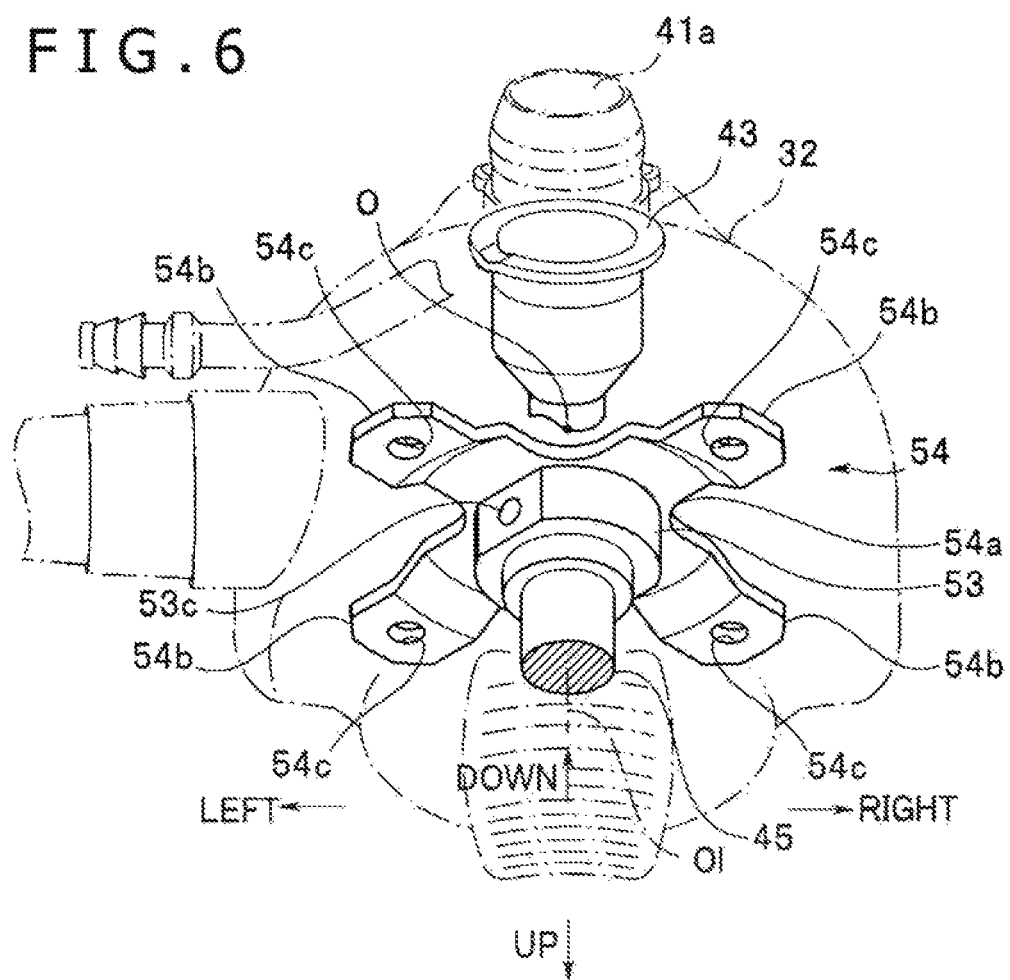
FIG. 6 is an explanatory diagram depicting the arrangement relationship between a wire pulling member and a cylinder.
Figure 10:
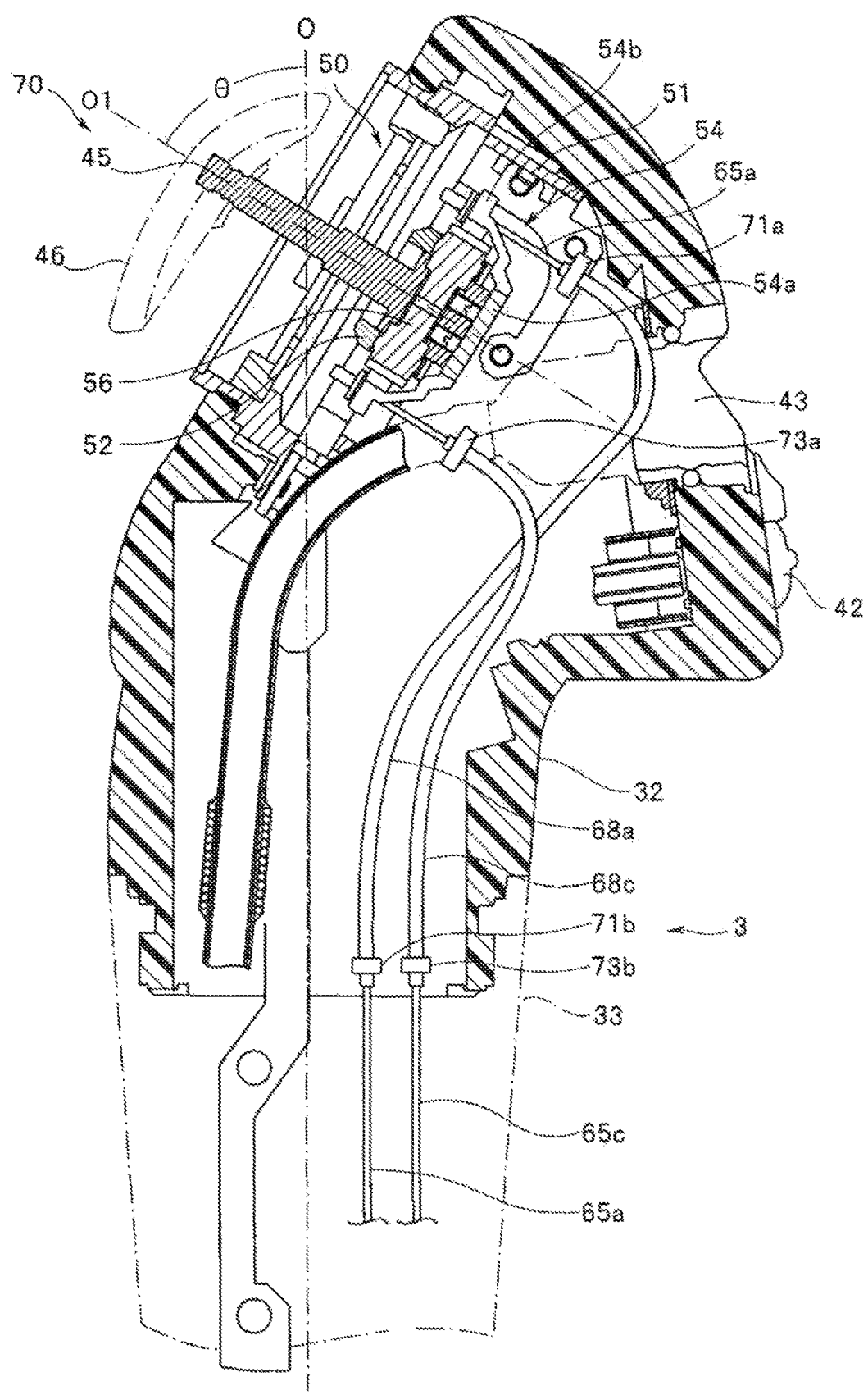
FIG. 10 is a sectional view of the major part of an operation unit.

As illustrated in FIG. 6, a cylinder 43 is disposed inside the operation unit main body 32. The suction valve 41 can be consecutively disposed with the cylinder 43. This cylinder 43 allows detachable fitting of the suction valve 41. The cylinder 43 is arranged centrally in the horizontal width direction of the operation unit main body 32 so that on the insertion axis "O", the cylinder 43 lies corresponding to the arrangement of the suction button 41a. The bending operation lever 45 is configured of a joystick-type lever that is tiltable in all directions including, for example, the up-down and left-right directions. This bending operation lever 45 is arranged on the side of the rear wall of the operation unit main body 32 at a position where the bending operation lever 45 is horizontally symmetrical. Described specifically, the bending operation lever 45 is arranged centrally in the horizontal wide direction of the operation unit main body 32 so that the bending lever 45 lies on the insertion axis "O". As illustrated in FIG. 10, the bending lever 45 is arranged with a lever axis O1 thereof extending at a preset angle θ with respect to the longitudinal direction of the operation unit main body 32 (the insertion axis "O").

As illustrated in FIGS. 7 to 10, a wire pulling mechanism 50 is consecutively disposed on the side of a proximal end of the bending operation lever 45 within the operation unit 3. As will be described subsequently herein, the individual bending operation wires 65a, 65b, 65c, and 65d are connected to the wire pulling mechanism 50 via a relay lever mechanism 60. The wire pulling mechanism 50 illustrated in FIGS. 7 to 10 includes a housing 51, a turnable frame 52, a base member 53, and a wire pulling member 54. The turnable frame 52 is turnably or rockably supported in the housing 51. The base member 53 is turnably or rockably supported in the turnable frame 52. The wire pulling member 54 is attachably disposed on the base member 53. The housing 51 is configured of a member having a substantially cylindrical shape. Through a circumferential wall of this housing 51, shank bores 51a are formed opposite to one another.

The turnable frame 52 is configured, for example, of a frame having a substantially rectangular shape. Mutually-opposing screw bores 52a are centrally formed in pair at opposite end portions in the direction of the longer sides through this turnable frame 52. In addition, mutually-opposing screw shank bores 52b are centrally formed in pair at opposite end portions in the direction of the shorter sides. Screws 55 is inserted in the respective shank bores 51a of the housing 51. The screws 55 are maintained in threaded engagement with the respective screw bores 52a, whereby the turnable frame 52 is supported on the housing 51 turnably. The base member 53 is configured of a member having a substantially cylindrical shape. On a central axis of the base member 53, the bending operation lever 45 is integrally formed. On the circumference of the base member 53, mutually-opposing flat portions 53b are formed in pair. Further, screw bores 53c are formed extending through the flat portions 53b. Screws 56 are inserted in the respective shank bores 52b of the turnable frame 52. The screws 56 are maintained in threaded engagement with the screw bores 53c, whereby the base member 53 is supported on the turnable frame 52 turnably. The base member 53 is supported on the housing 51 via the turnable frame 52 as described hereinbefore. The bending operation lever 45 is disposed integrally and consecutively with the base member 53. Therefore, the bending lever 45 can be tilted in a desired direction.

The wire pulling member 54 is configured of a plate-shaped member with arm portions 54b extending in four different directions from one another. More specifically, in this embodiment, the wire pulling member 54 is configured of a cruciform, plate-shaped member with the mutually-adjacent arm portions 54b set at angular intervals of 90 degrees. The wire pulling member 54 is attached at a central part 54a thereof on the base member 53 via screws 57. In other words, the bending operation lever 45 is connected to the wire pulling member 54 via the base member 53. As a consequence, the individual arm portions 54b are displaceable on the sides of distal ends thereof in response to tilting operation of the bending operation lever 45. On the sides of the distal ends of the individual arm portions 54b supported displaceable as described hereinbefore, wire fixing holes 54c are formed. The angle formed by the respective arm portions 54b is not limited to 90 degrees. For example, it is also possible to arbitrarily change the angle in a range of ±30 degrees based on these 90 degrees.

The wire pulling mechanism 50 is arranged so that it opposes the cylinder 43 in a front-to-rear relationship in the operation unit main body 32. In this arrangement, the wire pulling mechanism 50 is arranged at a position where the arm portions 54*b* is each angularly shifted within a range of 30 degrees to 60 degrees about the central axis O1 of the bending operation lever 45 relative to the corresponding up-down or left-right tilting direction set for the bending operation lever 45. The range can be set as 45 degrees. As a consequence, as illustrated in FIG. 6 and FIG. 7, for example, the wire pulling mechanism 50 is arranged in a state that the cylinder 43 can be seen between adjacent two of the arm portions 54*b* of the wire pulling member 54.

Here, description will be made in more detail hereinafter associated with the configuration of the four bending operation wires 65*a*, 65*b*, 65*c*, and 65*d* and four tubular members 68*a*, 68*b*, 68*c*, and 68*d* included in a bending operation device 70 of the present embodiment. The four bending operation wires are connected to the four arm portions 54*b* of the wire pulling member 54. The four tubular members 68*a*, 68*b*, 68*c*, and 68*d* change the extension direction of these four bending operation wires 65*a*, 65*b*, 65*c*, and 65*d* in the operation unit 3.

Figure 7:
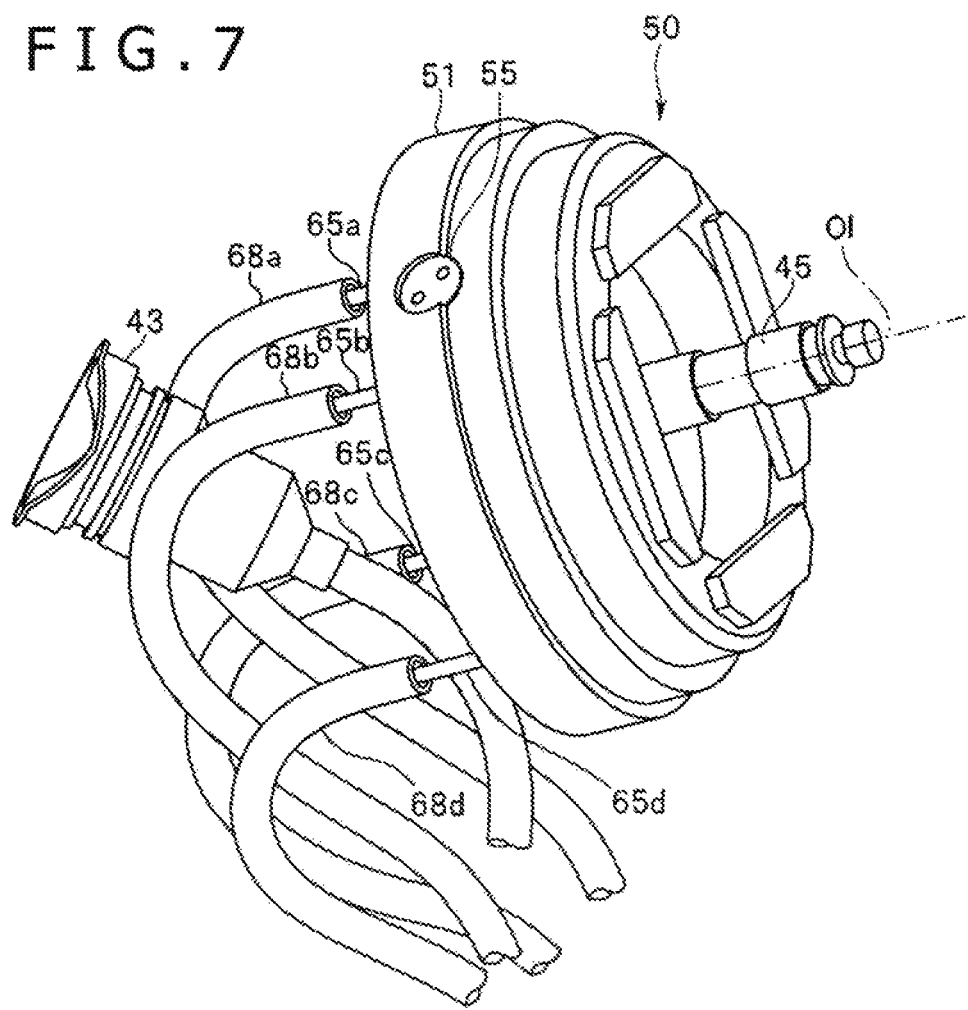
FIG. 7 is a perspective view depicting the arrangement relationship between a wire pulling mechanism and the cylinder.
Figure 8:
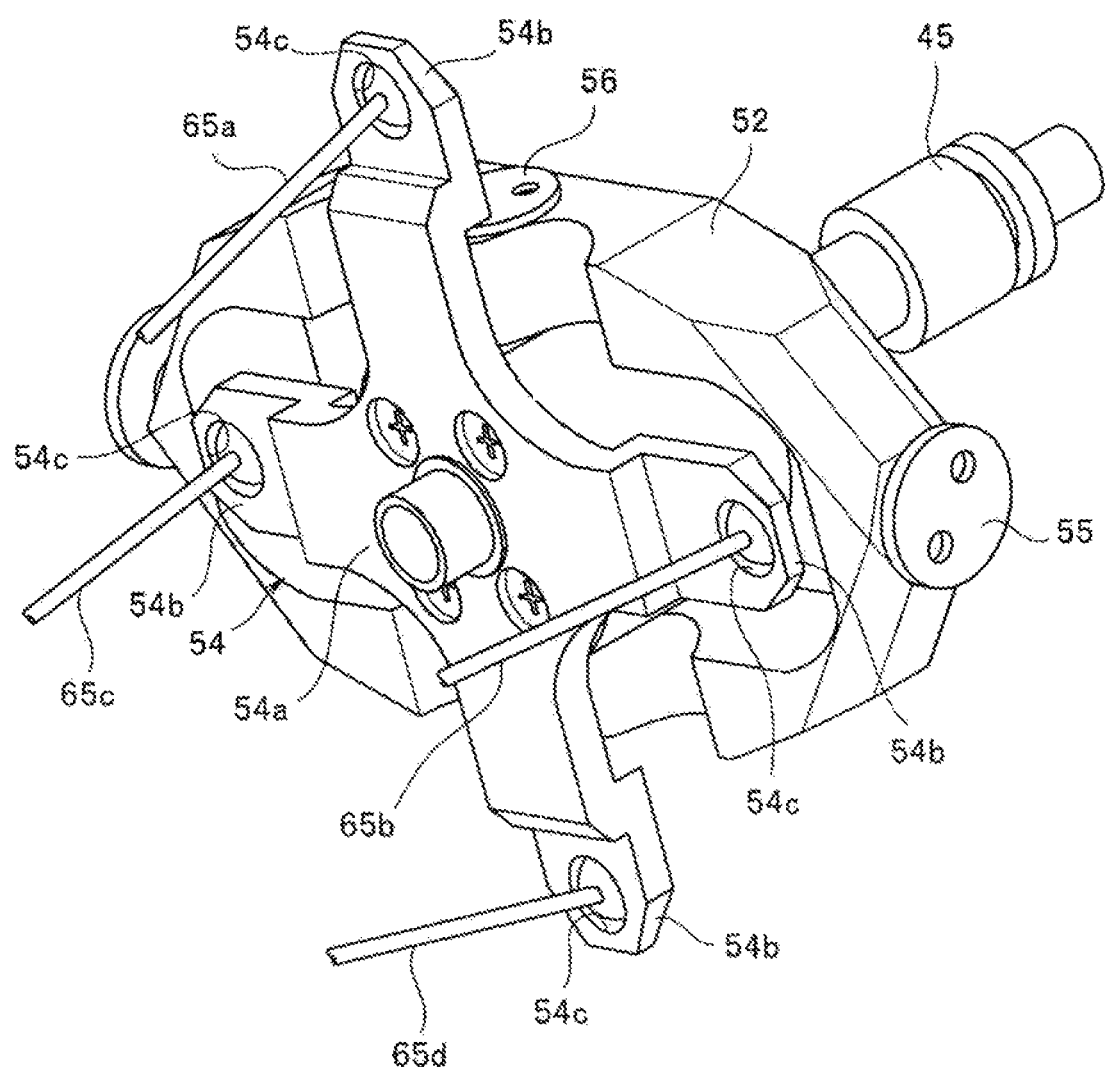
FIG. 8 is a perspective view depicting the internal structure of the wire pulling mechanism.
Figure 9:
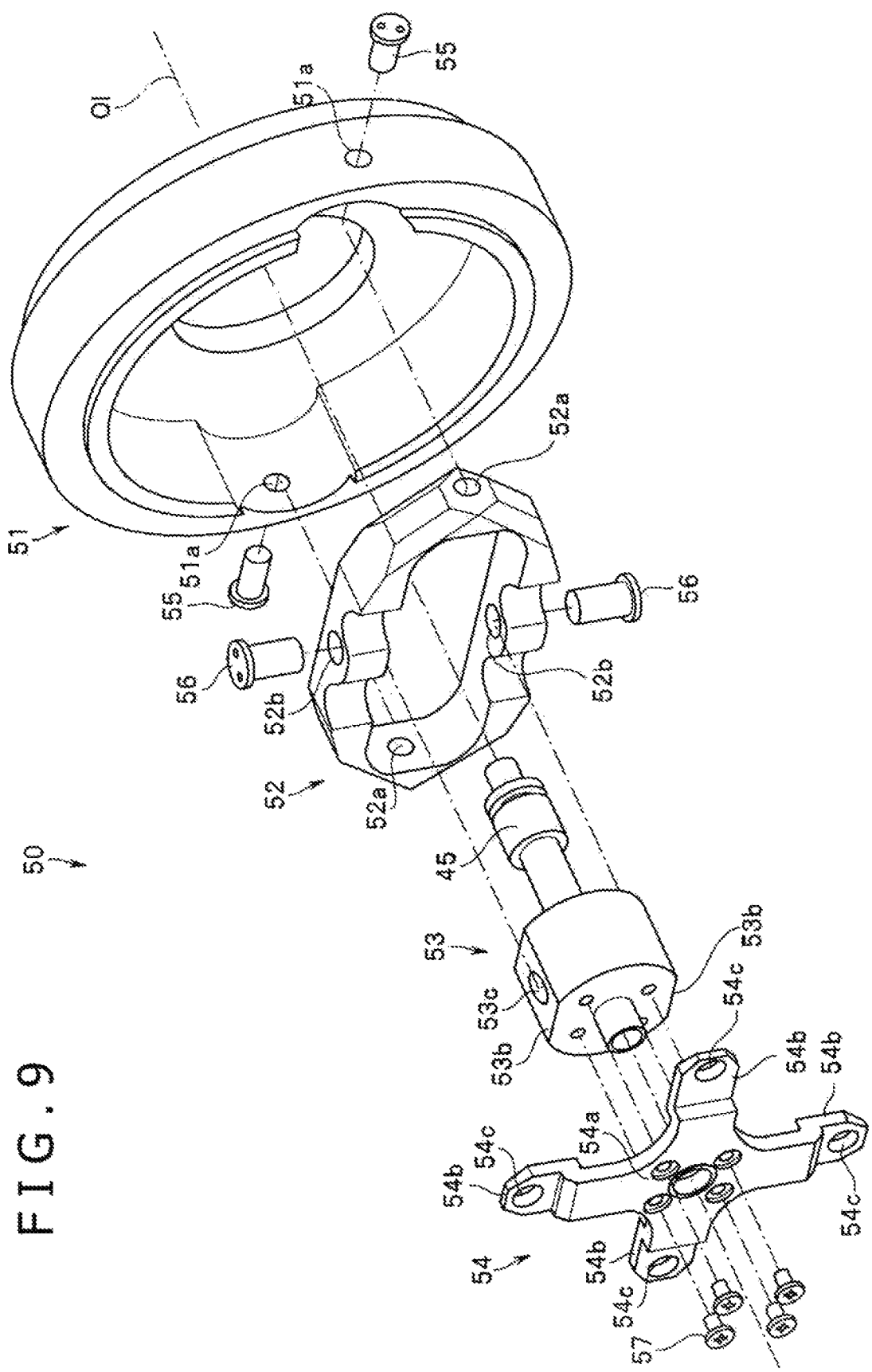
FIG. 9 is an exploded perspective view depicting the internal structure of the wire pulling mechanism.

As depicted in FIG. 6 and FIG. 7, the cylinder 43 is disposed on the front side and the wire pulling mechanism 50 is disposed on the rear side. Therefore, the wire pulling mechanism 50 of the bending operation device 70 is disposed opposed to the cylinder 43 position in the front-rear direction in the operation unit main body 32. The suction valve 41 is mounted to the cylinder 43. The four arm portions 54*b* of the wire pulling member 54 are disposed at positions resulting from rotational movement by 45° here around the central axis O1 of the bending operation lever 45. The central axis O1 of the bending operation lever 45 is the lever axis and has the predetermined angle θ with respect to the longitudinal direction of the operation unit main body 32, or direction of the insertion axis "O". Furthermore, here, the wire pulling mechanism 50 is disposed in the state in which the cylinder 43 is made to face the space between the two arm portions 54*b* on the upper side of the wire pulling member 54.

For this purpose, in the bending operation device 70, as depicted in FIG. 7 and FIG. 10, the four tubular members 68*a*, 68*b*, 68*c*, and 68*d* are soft tube bodies having flexibility. The respective bending operation wires 65*a*, 65*b*, 65*c*, and 65*d* are individually inserted in the four tubular members. Therefore, the respective bending operation wires 65*a*, 65*b*, 65*c*, and 65*d* may be kept from interfering with the cylinder 43 and so forth in the operation unit main body 32. The bending operation wires are connected to the four arm portions 54*b* of the wire pulling member 54. The cylinder 43 is incorporated objects.

These four tubular members 68*a*, 68*b*, 68*c*, and 68*d* are formed of a tightly-wound coil shape formed from a metal such as SUS or resin or a soft resin pipe such as a Teflon, which is registered trademark, tube.

Figure 11:
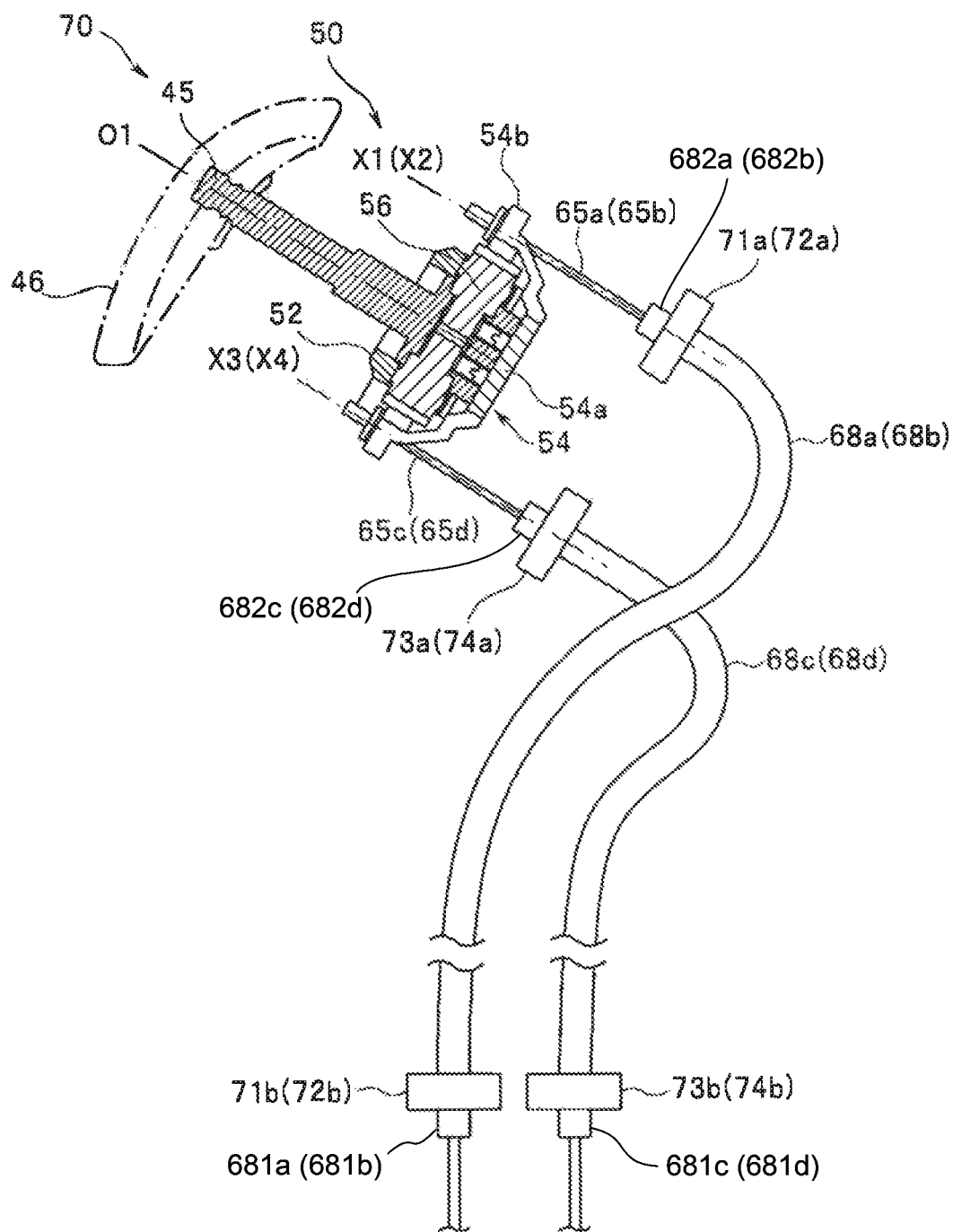
FIG. 11 is a sectional view for explaining a bending operation device.

As depicted in FIG. 10 and FIG. 11, these four tubular members 68*a*, 68*b*, 68*c*, and 68*d* are attached to attaching members 71*a*, 71*b*, 72*a*, 72*b*, 73*a*, 73*b*, 74*a*, and 74*b* in the operation unit main body 32 with the tubular members 68*a*, 68*b*, 68*c*, and 68*d* having predetermined looseness. Each of the four tubular members 68*a*, 68*b*, 68*c*, and 68*d* has one end part (proximal part) 682*a*, 682*b*, 682*c*, and 682*d* and opposite end part (tip portion) 681*a*, 681*b*, 681*c*, and 681*d*. Proximal parts 682*a*, 682*b*, 682*c*, and 682*d* at positions near the wire pulling mechanism 50 are attached to attaching members 71*a*, 72*a*, 73*a*, and 74*a*. The tip portions 681*a*, 681*b*, 681*c*, and 681*d* at positions of extension toward the distal side of the operation unit main body 32 are attached to the attaching members 71*b*, 72, 73*b*, and 74*b*.

In FIG. 11, two bending operation wires, two tubular members, and four attaching members that attach both ends of these two tubular members are diagrammatically represented. Furthermore, the respective attaching members 71*a*, 71*b*, 72*a*, 72*b*, 73*a*, 73*b*, 74*a*, and 74*b* are attached to the operation unit main body 32 or a frame or the like although details are not diagrammatically represented herein. Moreover, central axis O1 of the bending operation lever 45 is used as the lever axis. The central axis O1 has the predetermined angle θ with respect to the longitudinal direction of the operation unit main body 32, or direction of the insertion axis O. The four tubular members 68*a*, 68*b*, 68*c*, and 68*d* are disposed in such a manner as to be attached to four attaching members 71*a*, 72*a*, 73*a*, and 74*a* located near the wire pulling mechanism 50 in the operation unit main body 32 as depicted in FIG. 11. The neutral state of the bending operation lever 45 is set as the bendable part 7 to a substantially straight line in FIG. 10. When bending operation lever 45 is in the neutral state, wire axes X1, X2, X3, and X4 of the respective bending operation wires 65*a*, 65*b*, 65*c*, and 65*d* are each substantially parallel and oriented toward a respective one of the arm portions 54*b*.

In other words, the four tubular members 68*a*, 68*b*, 68*c*, and 68*d* are disposed at such positions that each of the wire axes X1, X2, X3, and X4 of the respective bending operation wires 65*a*, 65*b*, 65*c*, and 65*d* is falling on a respective one of the arm portions 54*b* at the same angle when the bending operation lever 45 is in the neutral state. The angle is, for example, angle within an error range of approximately ±20° with respect to the direction perpendicular to the arm portion 54*b*. Based on this arrangement, each of the wire axes X1, X2, X3, and X4 is substantially parallel. The central axis O1 of the bending operation lever 45 as the lever axis has the predetermined angle θ with respect to the longitudinal direction of the operation unit main body 32, or direction of the insertion axis O The neutral state is set as the bendable part 7 to a substantially straight line.

Furthermore, the disposing positions of the four tubular members 68*a*, 68*b*, 68*c*, and 68*d* are set by the attaching members 71*a*, 72*a*, 73*a*, and 74*a* in such a manner that (i) the respective wire axes X1, X2, X3, and X4 of the respective bending operation wires 65*a*, 65*b*, 65*c*, and 65*d* are incident in parallel to the central axis O1 and (ii) the respective wire axes X1, X2, X3, and X4 are a substantially orthogonal with respect to the extension direction of the arm portion 54*b*. Substantially orthogonal means the angle is ≈90 degrees with which the wire axes X1, X2, X3, and X4 are in a substantially perpendicular direction. The central axis O1 of the bending operation lever 45 is set as the lever axis herein.

That is, in the bending operation device 70, midway parts of the respective bending operation wires 65*a*, 65*b*, 65*c*, and 65*d* are inserted in the four tubular members 68*a*, 68*b*, 68*c*, and 68*d* in the operation unit main body 32. By these four tubular members 68*a*, 68*b*, 68*c*, and 68*d*, the respective bending operation wires 65*a*, 65*b*, 65*c*, and 65*d* are so set as to be substantially parallel and be oriented in parallel to the central axis O1 when the bending operation lever 45 is in the neutral state. The central axis O1 of the bending operation lever 45 is the lever axis substantially perpendicular with respect to the extension direction of the arm portions 54*b*. The bending operation lever 45 is provided to be tilted with the predetermined angle to the longitudinal direction of the operation unit main body 32, or direction of the insertion axis O. The neutral state is set as the bendable part 7 to a substantially straight line.

Therefore, in the endoscope 1, based on the four tubular members 68a, 68b, 68c, and 68d disposed in the bending operation device 70, the four bending operation wires 65a, 65b, 65c, and 65d that extend to the respective arm portions 54b are substantially parallel. The four bending operation wires 65a, 65b, 65c, and 65d are pulled and loosened corresponding to the amount of displacement of the respective arm portions 54b by tilt operation of the bending operation lever 45. The amount of pulling/loosening of the four bending operation wires 65a, 65b, 65c, and 65d becomes constant. Therefore, stable bending operation of the bendable part 7 can be carried out.

Moreover, the respective bending operation wires 65a, 65b, 65c, and 65d are each incident in parallel to the central axis O1 at a substantially orthogonal angle. The central axis O1 of the bending operation lever 45 is the lever axis. The substantially orthogonal angle is, namely, ≈90 degrees with which the bending operation wires 65a, 65b, 65c, and 65d are in a substantially perpendicular direction here with respect to the extension direction of the arm portion 54b. Thus, the size of the operation unit main body 32 does not need to be increased unnecessarily. Also, the size of the operation unit main body 32 for obtaining the angle for bending the bendable part 7 in a desired manner can be optimized. Therefore, increase in the size of the operation unit 3 can be prevented.

Furthermore, the respective bending operation wires 65a, 65b, 65c, and 65d are inserted in the respective tubular members 68a, 68b, 68c, and 68d that are soft and have flexibility from positions near the wire pulling mechanism 50. The respective tubular members 68a, 68b, 68c, and 68d can be disposed in a vacant space in the operation unit 3 in a bent state in such a manner as not to interfere with incorporated parts disposed in the operation unit 3. The incorporated parts are, for example, the cylinder 43 to which the suction valve 41 is mounted. Therefore, flexibility of the layout in the operation unit 3 is improved. Also, as a result of that, the size of the operation unit main body 32 does not need to be increased unnecessarily. Also, the size of the operation unit main body 32 for obtaining the angle for bending the bendable part 7 in a desired manner can be optimized. Therefore, increase in the size of the operation unit 3 can be prevented. In addition, incorporated parts do not get contact with the respective bending operation wires 65a, 65b, 65c, and 65d that advance and retreat. Damage to the incorporated parts can also be prevented.

According to the description hereinbefore, the endoscope including the bending operation device 70 of the present embodiment has a configuration with which (i) increase in the size of the operation unit 3 is prevented and (ii) the amount of pulling/loosening of the respective bending operation wires 65a, 65b, 65c, and 65d with respect to the amount of displacement by tilt of the bending operation lever 45 as a bending operation lever becomes constant and (iii) the amount of pulling/loosening of the respective bending operation wires 65a, 65b, 65c, and 65d with which the bendable part 7 is bent to the desired bending angle is stably obtained. Moreover, the endoscope including the bending operation device 70 has a configuration in which (i) incorporated objects disposed in the operation unit 3 do not get contact with the respective bending operation wires 65a, 65b, 65c, and 65d that advance and retreat, and (ii) damage to the incorporated objects can also be prevented.

In the description hereinbefore, the configuration is employed in which the respective bending operation wires 65a, 65b, 65c, and 65d are inserted in the respective tubular members 68a, 68b, 68c, and 68d that are soft and have flexibility. However, the respective tubular members 68a, 68b, 68c, and 68d may be hard members such as metal pipes or resin pipes deformed into such a shape as not to interfere with incorporated objects in the operation unit 3. In this case, as depicted in FIG. 12, for the respective tubular members 68a, 68b, 68c, and 68d, the fixing members 71b, 72b, 73b, and 74b that attach the respective other-end parts at positions of extension toward the distal side of the operation unit main body 32 do not need to be disposed.

Figure 12:
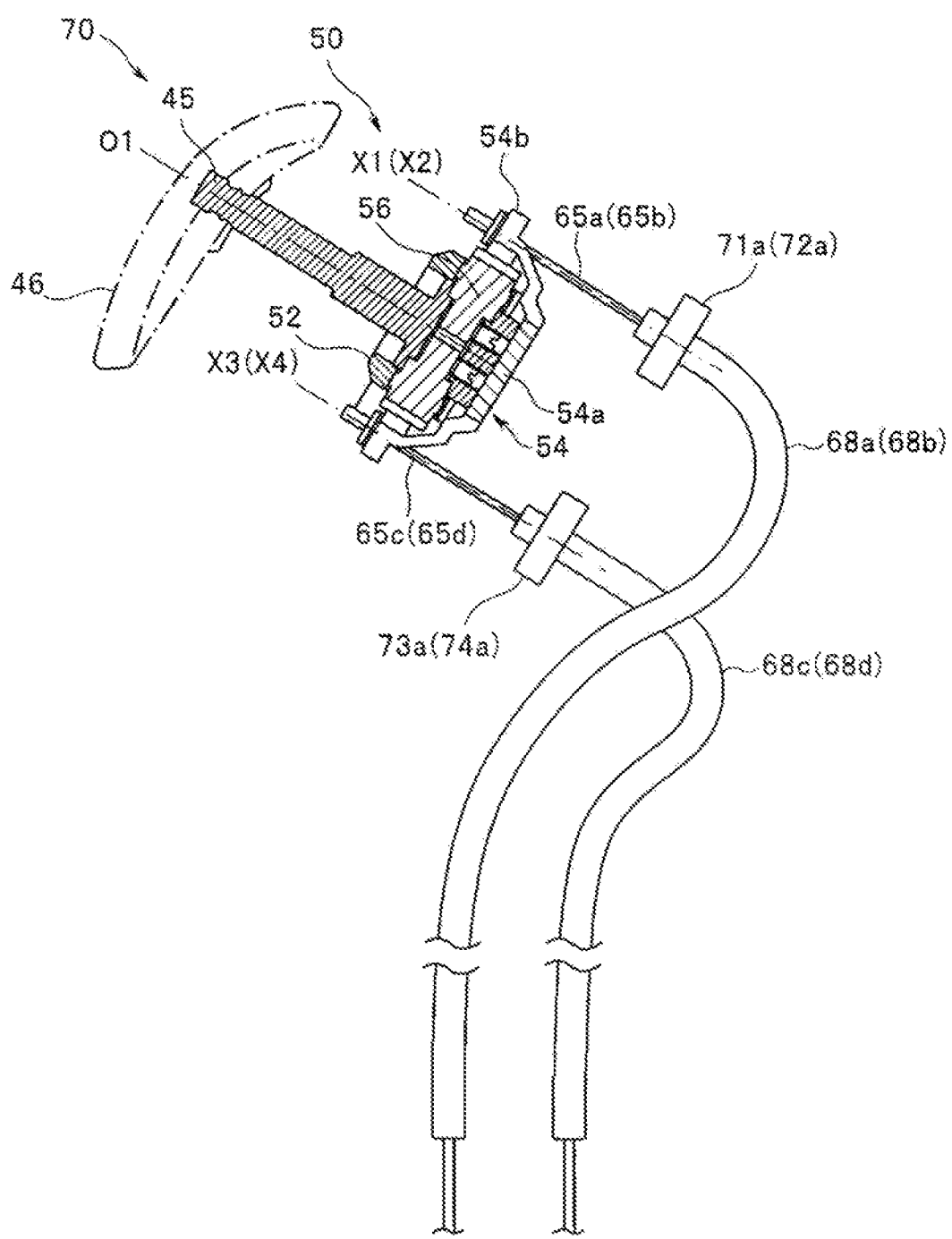
FIG. 12 is a sectional view for explaining a bending operation device of a modification example.

That is, as depicted in FIG. 12, if the four tubular members 68a, 68b, 68c, and 68d are hard members such as metal pipes or resin pipes, it suffices that only the one-end parts at positions near the wire pulling mechanism 50 be attached in the operation unit main body 32 by the attaching members 71a, 72a, 73a, and 74a.

The present disclosure is not limited to the respective embodiments described hereinbefore. Various modifications and changes are possible and they are also in the technical scope of the present invention. According to the present disclosure, it is possible to provide a bending operation device and an endoscope with which increase in the size of the operation unit is prevented and the amount of pulling/loosening of plural wires with respect to the amount of displacement by tilt of the bending operation lever becomes constant and the amount of pulling/loosening of the bending operation wire to bend the bendable part to a desired bending angle is stably obtained.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A bending operation device comprising:
   a bending operation lever tiltably supported to have an angle with respect to a longitudinal direction of an operation unit of an endoscope;
   a wire pulling member having a plurality of arm portions that are displaceable in conjunction with a tilt motion of the bending operation lever, the wire pulling member being disposed in the operation unit;
   a plurality of bending operation wires connected to the plurality of arm portions and configured to cause bending motion of a bendable part disposed in an insertion section of the endoscope by being pulled or loosened corresponding to displacement of the plurality of arm portions of the wire pulling member;
   a plurality of tubular members in each of which a respective one of the plurality of bending operation wires is inserted, the plurality of tubular members extending from respective tip portions to respective proximal parts disposed proximal of the respective tip portions, the tip portions and the proximal parts being disposed in the operation unit, the plurality of tubular members being:
      oriented in respective predetermined directions so as to orient the plurality of bending operation wires in the respective predetermined directions in the operation unit and guide the plurality of bending operation wires to the plurality of arm portions, and
      disposed in a vacant space in the operation unit in a bent state to change extension directions of the plurality of bending operation wires such that the plurality of bending operation wires extend: (i) directly from the plurality of arm portions in directions parallel to a central axis of the bending operation lever in a neutral position, and (ii) through a distal end portion of the operation unit that is connected to the insertion section in directions parallel to the longitudinal direction of the operation unit when the bending operation lever is in the neutral position, the central axis of the bending operation lever in the neutral position being transverse to the longitudinal direction of the operation unit, the bendable part being in a substantially straight line manner when the bending operation lever is in the neutral position;
   first attaching members that attach the tip portions of the plurality of tubular members in the operation unit in a manner so as to orient the tip portions in the respective predetermined directions; and
   second attaching members that attach the proximal parts of the plurality of tubular members in the operation unit in a manner such that the proximal parts extend in substantially parallel directions.

2. The bending operation device of claim 1, wherein the plurality of tubular members are disposed in the vacant space without interfering with incorporated objects in the operation unit.

3. The bending operation device of claim 1, wherein the plurality of tubular members are tube bodies that are made from soft and flexible material.

4. An endoscope comprising:
   an operation unit having a bending operation device being attached thereto, the bending operation device comprising:
      a bending operation lever tiltably supported to have an angle with respect to a longitudinal direction of the operation unit of the endoscope;
      a wire pulling member having a plurality of arm portions that are displaceable in conjunction with tilt motion of the bending operation lever, the wire pulling member being disposed in the operation unit;
      a plurality of bending operation wires connected to the plurality of arm portions and configured to cause bending motion of a bendable part disposed in an insertion section of the endoscope by being pulled or loosened corresponding to displacement of the plurality of arm portions of the wire pulling member;
      a plurality of tubular members in each of which a respective one of the plurality of bending operation wires is inserted, the plurality of tubular members extending from respective tip portions to respective proximal parts disposed proximal of the respective tip portions, the tip portions and the proximal parts being disposed in the operation unit, the plurality of tubular members being:
         oriented in respective predetermined directions so as to orient the plurality of bending operation wires in the respective predetermined directions in the operation unit and guide the plurality of bending operation wires to the plurality of arm portions, and
         disposed in a vacant space in the operation unit in a bent state to change extension directions of the plurality of bending operation wires such that the plurality of bending operation wires extend: (i) directly from the plurality of arm portions in directions parallel to a central axis of the bending operation lever in a neutral position, and (ii) through a distal end portion of the operation unit that is connected to the insertion section in directions parallel to the longitudinal direction of the operation unit when the bending operation lever is in the neutral position, the central axis of the bending operation lever in the neutral position being transverse to the longitudinal direction of the operation unit, the bendable part being in a substantially straight line manner when the bending operation lever is in the neutral position;

first attaching members that attach the tip portions of the plurality of tubular members in the operation unit in a manner so as to orient the tip portions in the respective predetermined directions; and second attaching members that attach the proximal parts of the plurality of tubular members in the operation unit in a manner such that the proximal parts extend in substantially parallel directions.

5. The endoscope of claim 4, wherein the plurality of tubular members are disposed in the vacant space without interfering with incorporated objects in the operation unit.

6. The endoscope of claim 4, wherein the plurality of tubular members are tube bodies that are made from soft and flexible material.

7. The bending operation device of claim 1, wherein the plurality of tubular members cause the plurality of bending operation wires to extend from the plurality of arm portions in directions substantially orthogonal to extension directions of the plurality of arm portions.

8. The bending operation device of claim 1, wherein the wire pulling member is disposed so as to be opposed to a cylinder to which a suction valve is mounted in a front-rear direction of the operation unit.

9. The bending operation device of claim 1, wherein a cylinder to which a suction valve is mounted is disposed in the operation unit so as to face a space between two arm portions of the plurality of arm portions of the wire pulling member.

10. The bending operation device of claim 1, wherein the tip portions of the plurality of tubular members extend at an angle with respect to extension directions of the respective proximal parts of the plurality of tubular members.

11. The endoscope of claim 4, wherein the plurality of tubular members cause the plurality of bending operation wires to extend from the plurality of arm portions in directions substantially orthogonal to extension directions of the plurality of arm portions.

12. The endoscope of claim 4, wherein the wire pulling member is disposed so as to be opposed to a cylinder to which a suction valve is mounted in a front-rear direction of the operation unit.

13. The endoscope of claim 4, wherein a cylinder to which a suction valve is mounted is disposed in the operation unit so as to face a space between two arm portions of the plurality of arm portions of the wire pulling member.

14. The endoscope of claim 4, wherein the tip portions of the plurality of tubular members extend at an angle with respect to extension directions of the respective proximal parts of the plurality of tubular members.

15. The bending operation device of claim 1, wherein a cylinder that is configured to detachably receive a suction valve is disposed inside the operation unit, and the wire pulling member is opposed to the cylinder in a front-rear direction of the operation unit, the front-rear direction being orthogonal to the longitudinal direction of the operation unit.

16. The endoscope of claim 4, wherein a cylinder that is configured to detachably receive a suction valve is disposed inside the operation unit, and the wire pulling member is opposed to the cylinder in a front-rear direction of the operation unit, the front-rear direction being orthogonal to the longitudinal direction of the operation unit.

* * * * *